United States Patent
Ravishankar et al.

(10) Patent No.: US 9,919,984 B2
(45) Date of Patent: Mar. 20, 2018

(54) PROCESS FOR THE PREPARATION OF ISOMERS OF XYLENE

(71) Applicant: HINDUSTAN PETROLEUM CORPORATION LIMITED, Mumbai (IN)

(72) Inventors: Raman Ravishankar, Bangalore (IN); Venkata Chalapathi Rao Peddy, Bangalore (IN); Venkateswarlu Choudary Nettem, Bangalore (IN); Ganapati Shanbhag, Bangalore (IN); Vijaykumar Marakatti, Bangalore (IN); Anand Halgeri, Bangalore (IN); Sriganesh Gandham, Bangalore (IN)

(73) Assignee: Hindustan Petroleum Corporation Limited, Mumbai, Maharashtra (IN)

( * ) Notice: Subject to any disclaimer, the term of this patent is extended or adjusted under 35 U.S.C. 154(b) by 0 days.

(21) Appl. No.: 14/913,825

(22) PCT Filed: Oct. 25, 2013

(86) PCT No.: PCT/IN2013/000651
§ 371 (c)(1),
(2) Date: Feb. 23, 2016

(87) PCT Pub. No.: WO2015/025327
PCT Pub. Date: Feb. 26, 2015

(65) Prior Publication Data
US 2016/0221893 A1    Aug. 4, 2016

(30) Foreign Application Priority Data
Aug. 23, 2013 (IN) .................. 2754/MUM/2013

(51) Int. Cl.
*C07C 2/86* (2006.01)
*B01J 29/08* (2006.01)
(Continued)

(52) U.S. Cl.
CPC ............. *C07C 2/864* (2013.01); *B01J 29/082* (2013.01); *B01J 29/084* (2013.01); *B01J 29/40* (2013.01);
(Continued)

(58) Field of Classification Search
CPC ....... C07C 2/86; C07C 2/864; C07C 2529/08; C07C 2529/70; C07C 2529/40
See application file for complete search history.

(56) References Cited

U.S. PATENT DOCUMENTS 3,965,208 A * 6/1976 Butter ................ B01J 29/40
                                                          208/DIG. 2
4,529,828 A    7/1985 Antos et al.
(Continued)

OTHER PUBLICATIONS

Jentoft, Thermal Treatment of Catalysts—Modern Methods in Heterogeneous Catalysis Research, Oct. 31, 2003, Handbook of Industrial Crystallization (http://www.fhi-berlin.mpg.de/acnew/department/pages/teaching/pages/teaching_wintersemester_2003_2004/jentoft_calcination_311003.pdf.*

(Continued)

*Primary Examiner* — In Suk C Bullock
*Assistant Examiner* — Youngsul Jeong
(74) *Attorney, Agent, or Firm* — Sand & Sebolt

(57) ABSTRACT

The present disclosure relates to a process for the preparation of isomers of xylene. The process includes method step of contacting an activated alkylation catalyst composite with toluene and methanol in the presence of an inert gas, at a temperature of 300 to 500° C. to obtain isomers of xylene. The alkylation catalyst composite used in accordance with the present disclosure comprises a molecular sieve loaded with at least one metal ion. The metal loaded on the molecular sieve is at least one alkali earth metal selected from the group consisting of barium, strontium, magnesium and calcium.

5 Claims, 2 Drawing Sheets

Figure 1:
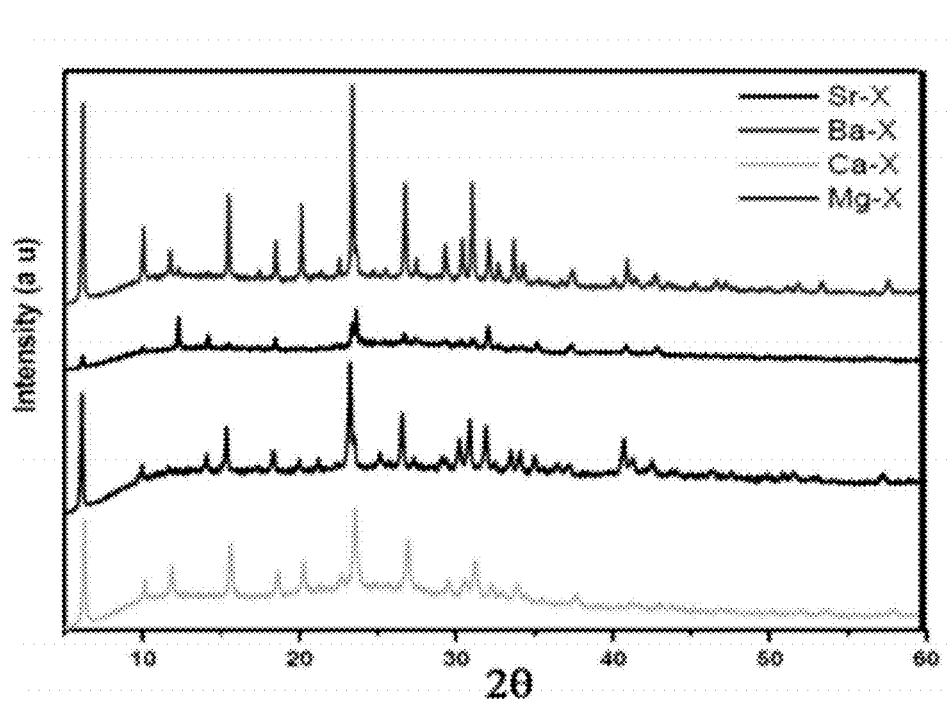

(51) Int. Cl.
  *B01J 29/40* (2006.01)
  *B01J 29/70* (2006.01)
(52) U.S. Cl.
  CPC ............ *B01J 29/7007* (2013.01); *B01J 29/08* (2013.01); *B01J 2229/186* (2013.01); *C07C 2/86* (2013.01); *C07C 2529/08* (2013.01); *C07C 2529/18* (2013.01); *C07C 2529/40* (2013.01); *C07C 2529/70* (2013.01); *C07C 2529/85* (2013.01); *Y02P 20/52* (2015.11)

(56) References Cited

U.S. PATENT DOCUMENTS

| | | |
|---|---|---|
| 5,994,603 A | 11/1999 | Mohr et al. |
| 6,689,929 B2 | 2/2004 | Williams et al. |
| 2002/0068844 A1 | 6/2002 | Williams et al. |
| 2005/0209492 A1 | 9/2005 | Ghosh et al. |
| 2010/0029467 A1 | 2/2010 | Inui et al. |
| 2012/0116139 A1 | 5/2012 | Inui et al. |

OTHER PUBLICATIONS

Venkatathri, Synthesis of high silica content silicoaluminophosphate-5 (SAPO-5) from non-aqueous medium using hexamethyleneimine template, 2005, Journal of Scientific and Industrial Research, vol. 64, pp. 509-514.*

"An Improved Method for the Synthesis of the Silicoaluminophosphate Molecular Sieves, SAPO-5, SAPO-11 and SAPO-31," A.K. Sinha, S. Sainkar, S. Sivasanker, National Chemical Laboratory, Pune 411 008, India, Received Nov. 25, 1998; accepted for publication Mar. 15, 1999.

"Synthesis of High Silica Content Silicoaluminophosphate-5 (SAPO-5) From Non-Aqueous Medium Using Hexamethyleneimine Template," N. Venkatathri, Catalysis Division, National Chemical Laboratory, Pune 411 008, Received Jan. 5, 2005; accepted May 16, 2005.

Martinez Sanchez, MC.; Corma Canos, A. (2011). "Inorganic Molecular Sieves: Preparation, Modification and Industrial Application in Catalytic Processes." Coordination Chemistry Reviews. 255(13-14): 1558-1580. doi:10.1016/j.ccr.2011.03.014.

* cited by examiner

PROCESS FOR THE PREPARATION OF ISOMERS OF XYLENE

FIELD OF THE DISCLOSURE

The present disclosure related to a process for the preparation of isomers of xylene.

BACKGROUND

Xylene is monocyclic aromatic compound with two methyl groups attached to the benzene ring. It exists in three isomeric forms: ortho, meta and para-xylene. Mostly, the individual isomers of xylene are separated and consumed in specific end-uses. Ortho-xylene is used primarily in the synthesis of phthalic acid, unsaturated polyester resins, alkyd resins; meta-xylene is key component for the synthesis of isophthalic acid and para-xylene is an important precursor to terephthalic acid and dimethyl terephthalate.

Usually, xylene is synthesized by the Friedel-Crafts alkylation reaction. However, alkylation catalysts such as $AlCl_3$, HF and $H_2SO_4$ employed in the Friedel-Crafts alkylation reaction have found to be environmentally hazardous. Therefore, in recent years, molecular sieve catalyst such as zeolites and silico aluminophosphate have attracted attention as alkylation catalysts, typically, due to their higher acidic properties, potential for regeneration and easy of separation from the reaction mixture.

However, use of such acidic alkylation catalysts in alkylation of toluene produces mix-xylenes, containing predominantly meta-xylene and para-xylene with very minor amount of ortho-xylene. While, the alkylation of toluene in the presence of basic alkylation catalyst such as Na—X-zeolite, Na—Y-zeolite, Na-beta-zeolite Na-ZSM-5 zeolite, Cs—X zeolite, Ba zeolite, and Rb—X zeolite predominantly, produces ethyl benzene and styrene due to side chain alkylation reaction.

Therefore, there is need to develop a simple and economic process for the preparation of isomers of xylene, particularly ortho-xylene using the basic alkylation catalyst.

OBJECTS

Some of the objects of the present disclosure, which at least one embodiment is able to achieve, are discussed herein below.

It is an object of the present disclosure to provide safe and economic process for the preparation of alkyl aromatic compounds using the basic alkylation catalyst composite.

It is another object of the present disclosure to provide safe and economic process for the preparation of isomers of xylene using the basic alkylation catalyst composite.

It is a further object of the present disclosure to provide a selective process for the preparation of ortho-xylene using the basic alkylation catalyst composite.

Other objects and advantages of the present disclosure will be more apparent from the following description when read in conjunction with the accompanying drawing, which are not intended to limit the scope of the present disclosure.

Definitions

As used in the present specification, the term 'molecular sieve' is used to define class of materials that exhibits selected sorption properties.

BRIEF DESCRIPTION OF THE ACCOMPANYING DRAWING

FIG. 1: illustrates the XRD for the alkylation catalyst composite of the present disclosure, in which A represents XRD for the Ca—X zeolite catalyst composite, B represents XRD for the Mg—X zeolite catalyst composite, C represents XRD for the Sr—X zeolite catalyst composite and D represents XRD for the Ba—X zeolite catalyst composite.

Figure 2:
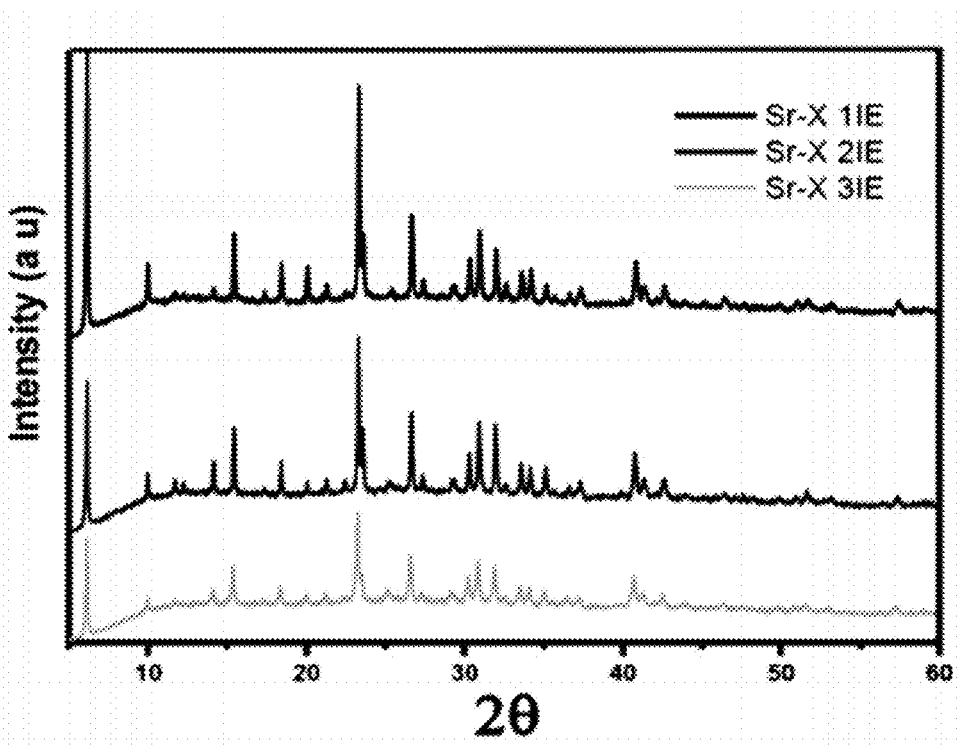

FIG. 2: illustrates the XRD for the Sr ion exchanged X zeolite catalyst composite of the present disclosure, in which:

A represents XRD for the Sr—X zeolite catalyst composite obtained after refluxing Na X-zeolite with strontium nitrate;

B represents XRD for the Sr—X zeolite catalyst composite obtained after repeating the method step of refluxing Na X-zeolite with strontium nitrate two times; and C represents XRD for the Sr—X zeolite catalyst composite obtained after repeating the method step of refluxing Na X-zeolite with strontium nitrate three times.

Figure 3:
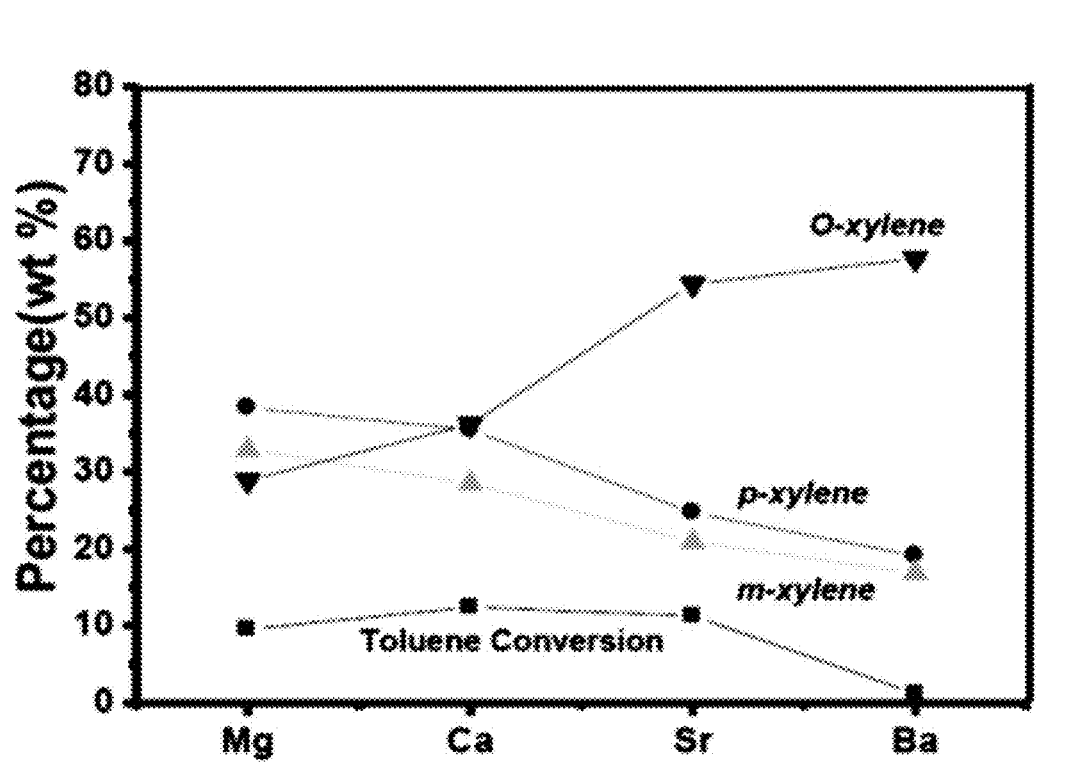

FIG. 3: illustrates amount of toluene alkylated using Mg—X zeolite catalyst composite, Ca—X zeolite catalyst composite, Sr—X zeolite catalyst composite and Ba—X zeolite catalyst composite of the present disclosure. In which A represents percent conversion of toluene, B represents percent alkylation of toluene to m-xylene, C represents percent alkylation of toluene to p-xylene and C represents percent alkylation of toluene to o-xylene.

SUMMARY

In accordance with one aspect of the present disclosure there is provided a process for the preparation of isomers of xylene; said process comprising the following steps:

i. obtaining an alkylation catalyst composite comprising a molecular sieve loaded with at least one metal ion;

ii. activating the alkylation catalyst composite at a temperature of 450 to 650° C. for a time period of 30 min to 2 hrs. in a reactor to obtain an activated alkylation catalyst composite; wherein the temperature for activating the alkylation catalyst composite is attained by heating the reactor at a rate of 4 to 10° C. per minute; and iii. contacting the activated alkylation catalyst composite with toluene and methanol in the presence of an inert gas, at a temperature of 300 to 500° C. to obtain a reaction mixture comprising isomers of xylene; wherein the mass of the ortho-xylene in said reaction mixture is greater than the individual mass of para-xylene and meta-xylene.

Typically, the molecular sieve is at least one zeolite selected from the group consisting of X-zeolite, Y-zeolite, beta-zeolite, ZSM-5 zeolite mordenite, ZSM-48, ZSM-22, ZSM-23, ZSM-57 and MCM-22.

Typically, the molecular sieve is at least one silico aluminophosphate (SAPO) selected from the group consisting of SAPO-5, SAPO-11, SAPO-17, SAPO-18, SAPO-44, SAPO-34 and SAPO-48.

Typically, the metal is at least one selected from the group consisting of group I elements, group II elements, group III elements, lanthanides and transition metals.

Typically, the metal is at least one selected from the group consisting of barium, strontium, magnesium and calcium.

Typically, the ratio of toluene to methanol ranges between 1:1 and 4:1.

Typically, the flow rate of toluene is maintained at a weight hourly space velocity of 1 to 5 per hr. of the activated alkylation catalyst composite.

Typically, the inert gas is at least one selected from the group consisting of nitrogen, argon and helium.

Typically, the flow rate of the inert gas ranges between 5 and 15 per min.

DETAILED DESCRIPTION

Alkylation of toluene using the acidic alkylation catalyst predominantly produces meta and para isomers of xylene, while the basic alkylation catalyst produces ethyl benzene and styrene. Therefore, with the view of increasing the yield of ortho-xylene, the inventors of the present disclosure have conducted several experiments and trials using number of alkylation catalysts. The inventors surprisingly found that the basic alkylation catalyst composite comprising molecular sieve loaded with at least one metal ion can selectively be used for the preparation of the isomers of xylene typically, ortho-xylene. Accordingly, the inventors of the present disclosure have developed a novel process for alkylation of toluene using the basic alkylation catalyst composite.

In accordance with one aspect of the present disclosure there is provided a process for the preparation of isomers of xylene.

In the initial step, the alkylation catalyst composite comprising a molecular sieve loaded with at least one metal ion is activated at a temperature of 450 to 650° C. for a time period of 30 min to 2 hrs. in a reactor to obtain an activated alkylation catalyst composite. The temperature for activating the alkylation catalyst composite is attained by heating the reactor at a rate of 4 to 10° C. per minute.

In accordance with one embodiment of the present disclosure the molecular sieve may be zeolite selected from the group consisting of X-zeolite, Y-zeolite, beta-zeolite, ZSM-5 zeolite mordenite, ZSM-48, ZSM-22, ZSM-23, ZSM-57, MCM-22 and mixtures thereof.

In accordance with another embodiment of the present disclosure the molecular sieve may be silico aluminophosphate (SAPO) selected from the group consisting of SAPO-5, SAPO-11, SAPO-17, SAPO-18, SAPO-44, SAPO-34, SAPO-48 and combinations thereof.

Typically, the metal loaded on molecular sieve is at least one selected from the group consisting of group I elements, group II elements, group III elements, lanthanides and transition metals. Typically, the metal loaded on molecular sieve is at least one selected from the group consisting of barium, strontium, magnesium and calcium.

In the next step, the activated alkylation catalyst composite is contacted with toluene and methanol at a temperature of 300 to 500° C. to obtain a reaction mixture comprising isomers of xylene as ortho-xylene, meta-xylene and para-xylene.

The mass of ortho-xylene present in the reaction mixture is greater the individual mass of para-xylene and meta-xylene.

The ratio of toluene to methanol is maintained in the range of 1:1 to 4:1 and the flow rate of toluene is maintained at a weight hourly space velocity of 1 to 5 per hr. of the activated catalyst. The method step of contacting the activated alkylation catalyst composite with toluene and methanol is carried out in the presence of inert gas selected from the group consisting of nitrogen, argon, helium and combinations thereof. The flow rate of inert gas is maintained in the range of 5 to 15 ml/min.

The present disclosure is further described in light of the following examples which are set forth for illustration purpose only and not to be construed for limiting the scope of the disclosure.

Example 1: Preparation of Ba—X Zeolite Using Na—X Zeolites

Step 1: Preparation of Na—X Zeolite:

5 gm of zeolite was treated with 20 liter of 0.5 M aqueous solution of sodium nitrate ($NaNO_3$) under reflux for 8 hrs, followed by filtration, washing with water until the filtrate became free from sodium ions, drying at 120° C. for 8 h and calcination at 550° C. for 4 h in air. The ratio of aqueous solution of sodium nitrate to zeolite was maintained as 10:1. The procedure was repeated twice to obtain Na—X zeolites.

Step II—Preparation of an Alkylation Catalyst Composite (Ba—X Zeolite Catalyst Composite) Using Na—X Zeolite:

The Na—X zeolite was treated with 0.5 M of barium acetate solution using the method described in step I to obtain a Ba—X zeolite. In this process the sodium nitrate is replaced with barium acetate.

Step III—Preparation of Isomers of Xylene Using Ba—X Zeolite Catalyst Composite:

2 g of Ba—X zeolites catalyst composite of 0.8 to 1.7 mm mesh size was taken in a quartz micro reactor. Temperature in the reactor was ramped with 8° C./min to 500° C. Catalyst was activated in presence of air for a time period of 1 hr. Then the temperature of the activated catalyst was brought down to 420° C. Feed of Toluene and methanol (4:1) with a weight hourly space velocity (WHSV) (toluene)=2.5 $h^{-1}$ was fed into pre-heater with a syringe pump and nitrogen was fed with calibrated Rota meter with the flow of 10 ml/min. Products were cooled in condenser maintained at 2° C. and products are collected in gas liquid separator maintained at 5° C. Products were analyzed through gas chromatograph equipped with FID using a carbowax (polar) column of 60 m×0.25 um×0.25 mm.

TABLE 1

|  | 1 hr. | 2 hrs. | 3 hrs. | 4 hrs. |
| --- | --- | --- | --- | --- |
| Product distribution (wt %) | | | | |
| Benzene | 0.01 | 0.007 | 0.04 | 0.005 |
| Toluene | 98.60 | 98.67 | 98.78 | 98.93 |
| Ethyl benzene | 0.03 | 0.024 | 0.024 | 0.023 |
| p-xylene | 0.26 | 0.26 | 0.23 | 0.21 |
| m-xylene | 0.25 | 0.23 | 0.20 | 0.19 |
| o-xylene | 0.78 | 0.77 | 0.68 | 0.60 |
| Styrene | 0.01 | 0.01 | 0.01 | 0.005 |
| Trimethyl benzene | 0.02 | 0.02 | 0.02 | 0.02 |
| Others | 0.03 | 0.02 | 0.01 | 0.01 |
| Performance (wt %) | | | | |
| Toluene conversion | 1.4 | 1.3 | 1.2 | 1.1 |
| Styrene selectivity | 0.8 | 0.8 | 1 | 0.4 |
| Ethyl benzene selectivity | 2 | 2.1 | 2 | 2 |
| Mixed xylene selectivity | 92.3 | 95.4 | 92.3 | 90.9 |

Example 2: Preparation of an Alkylation Catalyst Composite (Ca—X Zeolite Catalyst Composite) Using Na—X Zeolite The Na—X zeolite was treated with 0.5 M of calcium nitrate ($CaNO_3$) solution using the step-I of Example 1 to obtain a Ca—X zeolite. In this process sodium nitrate is replaced with calcium nitrate.

Preparation of Isomers of Xylene Using Ca—X Zeolite Catalyst Composite:

The isomers of xylene were prepared by employing the procedure described in the Example 1. In this process Ba—X zeolites catalyst composite is replaced with Ca—X zeolite catalyst composite

TABLE 2

|  | 1 hr. | 2 hrs. | 3 hrs. | 4 hrs. |
|---|---|---|---|---|
| Product distribution (wt %) | | | | |
| Benzene | 0.26 | 0.36 | 0.44 | 0.51 |
| Toluene | 89.43 | 87.59 | 86.94 | 87.99 |
| Ethyl benzene | 0.033 | 0.062 | 0.08 | 0.08 |
| p-xylene | 2.55 | 3.35 | 3.66 | 3.49 |
| m-xylene | 2.28 | 2.70 | 2.93 | 2.83 |
| o-xylene | 3.98 | 3.43 | 3.06 | 2.65 |
| Styrene | 0.08 | 0.13 | 0.14 | 0.12 |
| Trimethyl benzene | 0.87 | 1.26 | 1.30 | 1.08 |
| Others | 0.51 | 1.11 | 1.46 | 1.23 |
| Performance (wt %) | | | | |
| Toluene conversion | 10.57 | 12.42 | 13.07 | 12.02 |
| Styrene selectivity | 0.7 | 1.0 | 1.0 | 1.0 |
| Ethyl benzene selectivity | 0.3 | 0.5 | 0.6 | 0.7 |
| Mixed xylene selectivity | 83.1 | 76.24 | 73.75 | 74.65 |

Example 3: Preparation of the Alkylation Catalyst Composite (Sr—X Zeolite Catalyst Composite) Using Na—X Zeolites The Na—X zeolite was treated with 0.5 M of Strontium nitrate $(Sr(NO_3)_2)$ solution using Step-I of Example 1 to obtain a Sr—X zeolite. In this process sodium nitrate is replaced with Strontium nitrate.

Preparation of Isomers of Xylene Using Sr—X Zeolite Catalyst Composite:

The isomers of xylene were prepared by employing the procedure described in the Example 1. Feed of toluene and methanol (2:1) with a weight hourly space velocity (WHSV) of 2.5 $h^{-1}$ was fed into pre-heater and the nitrogen was fed at a flow rate of 10 ml per min. In this process Ba—X zeolite catalyst composite is replaced with Sr—X zeolites catalyst composite wherein the amount of catalyst was 2 g. The results so obtained are shown herein table 3 below.

TABLE 3

|  | 1 hr. | 2 hr | 3 hr | 4 hr |
|---|---|---|---|---|
| Product distribution (wt %) | | | | |
| Benzene | 0.06 | 0.039 | 0.0238 | 0.04 |
| Toluene | 83.46 | 85.28 | 85.42 | 86.30 |
| Ethyl benzene | 0.02 | 0.03 | 0.04 | 0.04 |
| p-Xylene | 2.95 | 2.65 | 2.70 | 2.69 |
| m-Xylene | 2.34 | 2.11 | 2.12 | 2.09 |
| o-Xylene | 6.028 | 5.05 | 4.74 | 4.44 |
| Trimethyl benzene | 1.82 | 1.55 | 1.53 | 1.44 |
| Others | 3.30 | 3.26 | 3.40 | 3.0 |
| Performance (wt %) | | | | |
| Toluene conversion | 16.54 | 14.72 | 14.58 | 13.75 |
| Mixed xylene selectivity | 68.43 | 66.64 | 65.57 | 67.05 |
| p-Xylene selectivity | 26.06 | 27.01 | 28.24 | 29.18 |
| m-Xylene selectivity | 20.68 | 21.51 | 22.18 | 22.67 |
| o-Xylene selectivity | 53.26 | 51.48 | 49.58 | 48.16 |

Example 4: Preparation of the Alkylation Catalyst Composite (Sr—X Zeolite Catalyst Composite) Using Na—X Zeolites The Na—X zeolite was treated with 0.5 M of Strontium nitrate $(Sr(NO_3)_2)$ solution using Step-I of Example 1 to obtain a Sr—X zeolite. In this process sodium nitrate is replaced with Strontium nitrate.

Preparation of Isomers of Xylene Using Sr—X Zeolite Catalyst Composite:

The isomers of xylene were prepared by employing the procedure described in the Example 1. In this process Ba—X zeolite catalyst composite is replaced with Sr—X zeolites catalyst composite.

TABLE 4

|  | 1 hr. | 2 hrs. | 3 hrs. | 4 hrs. |
|---|---|---|---|---|
| Product distribution (wt %) | | | | |
| Benzene | 0.058 | 0.054 | 0.094 | 0.10 |
| Toluene | 88.70 | 89.17 | 87.97 | 88.77 |
| Ethyl benzene | 0.022 | 0.03 | 0.037 | 0.05 |
| p-xylene | 2.48 | 2.21 | 2.48 | 2.43 |
| m-xylene | 2.10 | 1.86 | 2.03 | 1.93 |
| o-xylene | 5.46 | 4.62 | 4.33 | 3.87 |
| Styrene | 0.06 | 0.10 | 0.10 | 0.14 |
| Trimethyl benzene | 1.1 | 1.04 | 1.23 | 1.12 |
| Others | 0.97 | 0.91 | 1.72 | 1.60 |
| Performance (wt %) | | | | |
| Toluene conversion | 11.3 | 10.83 | 12.04 | 11.23 |
| Styrene selectivity | 0.5 | 0.1 | 0.8 | 1.2 |
| Ethyl benzene selectivity | 0.1 | 0.2 | 0.3 | 0.4 |
| Mixed xylene selectivity | 88.8 | 80 | 73.3 | 73.1 |

Example 5: Preparation of the Alkylation Catalyst Composite (Sr—X Zeolite Catalyst Composite) Using Na—X Zeolites The Na—X zeolite was treated with 0.5 M of Strontium nitrate $(Sr(NO_3)_2)$ solution using Step-I of Example 1 to obtain a Sr—X zeolite. In this process sodium nitrate is replaced with Strontium nitrate.

Preparation of Isomers of Xylene Using Sr—X Zeolite Catalyst Composite:

The isomers of xylene were prepared by employing the procedure described in the Example 1. Feed of toluene and methanol (6:1) with a weight hourly space velocity (WHSV) of 2.5 h$^{-1}$ was fed into pre-heater and the nitrogen was fed at a flow rate of 10 ml per min. In this process Ba—X zeolite catalyst composite is replaced with Sr—X zeolites catalyst composite wherein the amount of catalyst was 2 g. The results so obtained are shown herein table 5 below.

TABLE 5

|  | 1 hr | 2 hr | 3 hr | 4 hr |
|---|---|---|---|---|
| Product distribution (wt %) | | | | |
| Benzene | 0.019 | 0.014 | 0.013 | 0.012 |
| Toluene | 94.19 | 95.36 | 95.77 | 95.97 |
| Ethyl benzene | 0.01 | 0.01 | 0.01 | 0.01 |
| p-Xylene | 1.089 | 0.87 | 0.82 | 0.76 |
| m-Xylene | 0.91 | 0.74 | 0.70 | 0.65 |
| o-Xylene | 2.75 | 2.22 | 2.06 | 1.90 |
| Trimethyl benzene | 0.38 | 0.26 | 0.24 | 0.22 |
| Others | 0.63 | 0.50 | 0.37 | 0.45 |
| Performance (wt %) | | | | |
| Toluene conversion | 5.80 | 4.64 | 4.23 | 4.00 |
| Mixed xylene selectivity | 81.88 | 82.54 | 84.63 | 82.75 |
| p-Xylene selectivity | 22.93 | 22.72 | 22.91 | 22.96 |
| m-Xylene selectivity | 19.16 | 19.32 | 19.55 | 19.64 |
| o-Xylene selectivity | 57.91 | 57.96 | 57.54 | 57.40 |

Example 6: Preparation of the Alkylation Catalyst Composite (Sr—X Zeolite Catalyst Composite) Using Na—X Zeolites The Na—X zeolite was treated with 0.5 M of Strontium nitrate (Sr(NO$_3$)$_2$) solution using Step-I of Example 1 to obtain a Sr—X zeolite. In this process sodium nitrate is replaced with Strontium nitrate.

Preparation of Isomers of Xylene Using Sr—X Zeolite Catalyst Composite:

The isomers of xylene were prepared by employing the procedure described in the Example 1. Feed of toluene and methanol (8:1) with a weight hourly space velocity (WHSV) of 2.5 h$^{-1}$ was fed into pre-heater and the nitrogen was fed at a flow rate of 10 ml per min. In this process Ba—X zeolite catalyst composite is replaced with Sr—X zeolites catalyst composite wherein the amount of catalyst was 2 g. The results so obtained are shown herein table 6 below.

TABLE 6

|  | 1 hr | 2 hr | 3 hr | 4 hr |
|---|---|---|---|---|
| Product distribution (wt %) | | | | |
| Benzene | 0.03 | 0.02 | 0.01 | 0.01 |
| Toluene | 96.29 | 96.82 | 96.48 | 96.52 |
| Ethyl benzene | 0.01 | 0.01 | 0.01 | 0.01 |
| p-Xylene | 0.70 | 0.60 | 0.66 | 0.68 |
| m-Xylene | 0.63 | 0.54 | 0.58 | 0.52 |
| o-Xylene | 1.77 | 1.50 | 1.60 | 1.62 |
| Trimethyl benzene | 0.23 | 0.19 | 0.22 | 0.20 |
| Others | 0.31 | 0.30 | 0.41 | 0.40 |
| Performance (wt %) | | | | |
| Toluene conversion | 3.71 | 3.18 | 3.52 | 3.48 |
| Mixed xylene selectivity | 83.56 | 83.02 | 80.68 | 81.03 |
| p-Xylene selectivity | 22.58 | 22.73 | 23.24 | 24.11 |
| m-Xylene selectivity | 20.32 | 20.45 | 20.42 | 18.44 |
| o-Xylene selectivity | 57.10 | 56.82 | 56.34 | 57.45 |

Example 7: Preparation of the Alkylation Catalyst Composite (Sr—X Zeolite Catalyst Composite) Using Na—X Zeolites The Na—X zeolite was treated with 0.5 M of Strontium nitrate (Sr(NO$_3$)$_2$) solution using Step-I of Example 1 to obtain a Sr—X zeolite. In this process sodium nitrate is replaced with Strontium nitrate.

Preparation of Isomers of Xylene Using Sr—X Zeolite Catalyst Composite:

The isomers of xylene were prepared by employing the procedure described in the Example 1. Feed of toluene and methanol (4:1) with a weight hourly space velocity (WHSV) of 1.0 h$^{-1}$ was fed into pre-heater and the nitrogen was fed at a flow rate of 10 ml per min. In this process Ba—X zeolite catalyst composite is replaced with Sr—X zeolites catalyst composite wherein the amount of catalyst was 2 g. The results so obtained are shown herein table 7 below.

TABLE 7

|  | 1 hr | 2 hr | 3 hr | 4 hr |
|---|---|---|---|---|
| Product distribution (wt %) | | | | |
| Benzene | 0.21 | 0.08 | 0.11 | 0.09 |
| Toluene | 85.07 | 87.47 | 86.01 | 87.23 |
| Ethyl benzene | 0.02 | 0.02 | 0.02 | 0.02 |
| p-Xylene | 2.88 | 2.29 | 2.65 | 2.40 |
| m-Xylene | 2.86 | 2.00 | 2.34 | 2.07 |
| o-Xylene | 5.69 | 4.55 | 5.23 | 4.47 |
| Trimethyl benzene | 1.56 | 1.4 | 1.54 | 1.42 |
| Others | 1.66 | 2.17 | 2.06 | 2.26 |
| Performance (wt %) | | | | |
| Toluene conversion | 14.93 | 12.53 | 14.0 | 12.77 |
| Mixed xylene selectivity | 76.56 | 70.55 | 73.00 | 70.01 |
| p-Xylene selectivity | 25.20 | 25.90 | 25.93 | 26.85 |
| m-Xylene selectivity | 25.02 | 22.62 | 22.90 | 23.15 |
| o-Xylene selectivity | 49.78 | 51.47 | 51.17 | 50.0 |

The catalytic activity of Sr—X zeolite catalyst composite was compared with the catalytic activity of Mg—X zeolite catalyst composite, Ca—X zeolite catalyst composite and Ba—X zeolite. (shown in FIG. 3 and Table 8)

TABLE 8

Percent alkylation of toluene using the alkylation catalyst comprising Sr metal ion loaded zeolites.

| | Performance (wt %) | | | |
|---|---|---|---|---|
|  | Sr-X | Sr-Y | Sr-ZSM-5 | Sr-Beta |
| Toluene conversion | 10.8 | 17.3 | 16 | 41.4 |
| Mixed xylene selectivity | 80.0 | 71.5 | 74.8 | 65.4 |
| p-xylene selectivity | 25.4 | 31.1 | 36.7 | 24.0 |
| m-xylene selectivity | 21.3 | 40.6 | 50.4 | 52.9 |
| o-xylene selectivity | 53.2 | 28.3 | 15.4 | 23 |

Characterization

XRD Analysis:

1. The phase purity and crystalline properties of zeolite catalysts composite (Ca—X zeolite catalyst composite, Mg—X zeolite catalyst composite, Sr—X zeolite catalyst composite and Ba—X zeolite catalyst composite) were determined by the X-ray diffractometer instrument with Cu Kα Source (λ=1.542 Å. The zeolite catalysts were analyzed in the 2θ range of 5° to 70° with scanning rate of 0.02 degrees per second at temperature of 25° C. XRD pattern for zeolite catalysts shown in FIG. 1.

2. The phase purity and crystalline properties of Sr ion exchanged X zeolite was determined by the X-ray diffractometer instrument with Cu Kα Source (λ=1.542 A°). The zeolite catalyst was analyzed in the 2θ range of 10 to 70° with scanning rate of 0.02 degrees per second at temperature of 25° C. XRD pattern for Sr X zeolite shown in FIG. 2.

Atomic Absorption Spectrometry (AAS):

The percent sodium (Na) exchanged with the metal ions selected from the group consisting of magnesium (Mg), calcium (Ca), strontium (Sr) and barium (Ba) was determined by Atomic Absorption Spectrometry.

TABLE 9

| S. No | Catalyst | Ion exchange (wt %) |
|---|---|---|
| 1. | Na-X zeolite | 0.0 |
| 2 | Mg-X zeolite | 68.7 |
| 3. | Ca-X zeolite | 92.8 |
| 4. | Sr-X zeolite | 96.1 |
| 5. | Ba-X zeolite | 93.8 |

Comparative Example 1

The isomers of xylene were prepared by employing the procedure described in the Example 1. In this process Ba—X zeolite catalyst composite is replaced with commercially available Na—X zeolite catalyst.

TABLE 10

| | 1 hr. | 2 hrs. | 3 hrs. | 4 hrs. |
|---|---|---|---|---|
| Product distribution (wt %) | | | | |
| Benzene | 0.023 | 0.010 | 0.008 | 0.008 |
| Toluene | 94.94 | 96.75 | 96.81 | 97.05 |
| Ethyl benzene | 0.067 | 0.077 | 0.08 | 0.09 |
| p-xylene | 0.715 | 0.61 | 0.65 | 0.60 |
| m-xylene | 0.63 | 0.51 | 0.53 | 0.50 |
| o-xylene | 1.69 | 1.49 | 1.57 | 1.46 |
| Styrene | 0.05 | 0.09 | 0.059 | 0.05 |
| Trimethyl benzene | 0.125 | 0.07 | 0.099 | 0.09 |
| $C_9$-$C_{10}$ aromatics | 1.74 | 0.39 | 0.20 | 0.16 |
| Performance (wt %) | | | | |
| Toluene conversion | 5.0 | 3.25 | 3.2 | 3.0 |
| Styrene selectivity | 1.0 | 2.86 | 1.8 | 1.5 |
| Ethyl benzene selectivity | 1.34 | 2.3 | 2.6 | 2.9 |
| Mixed xylene selectivity | 60.76 | 79.38 | 85 | 85 |

Comparative Example 2

The isomers of xylene were prepared by employing the procedure described in the Example 1. In this process Ba—X zeolite catalyst composite is replaced with commercially available H-Beta and H-ZSM-5. The amount of the xylene produced by the Sr—X zeolite composite was then compared with amount of the xylene produced using H-Beta and HZSM-5

TABLE 11

| | Sr-X zeolite catalyst composite of the present disclosure | H-BETA | H-ZSM-5 |
|---|---|---|---|
| Product distribution (wt %) | | | |
| Benzene | 0.054 | 9.03 | 7.30 |
| Toluene | 89.17 | 68.66 | 60.24 |
| Ethyl benzene | 0.03 | 0.28 | 0.35 |
| p-xylene | 2.21 | 5.08 | 6.05 |
| m-xylene | 1.85 | 9.95 | 13.45 |
| o-xylene | 4.61 | 3.93 | 5.98 |
| Others | 0.91 | 3.03 | 6.6 |
| Conversion and selectivity (wt %) | | | |
| Benzene | 0.054 | 9.03 | 7.30 |
| Toluene conversion | 10.83 | 31.34 | 39.76 |
| Mixed xylene selectivity | 80 | 60.54 | 63.9 |
| p-xylene selectivity | 25.4 | 26.4 | 23.5 |
| m-xylene selectivity | 21.3 | 52.7 | 52.89 |
| o-xylene selectivity | 52.9 | 20.8 | 23.5 |

Example 8: Preparation of the Alkylation Catalyst Composite (Sr—X Zeolite Catalyst Composite) Using Na—X Zeolites The Na—X zeolite was treated with 0.5 M of Strontium nitrate ($Sr(NO_3)_2$) solution using Step-I of Example 1 to obtain a Sr—X zeolite. In this process sodium nitrate is replaced with Strontium nitrate.

Preparation of Isomers of Xylene Using Sr—X Zeolite Catalyst Composite:

The isomers of xylene were prepared by employing the procedure described in the Example 1. Feed of toluene and methanol (4:1) with a weight hourly space velocity (WHSV) of 4.0 $h^{-1}$ was fed into pre-heater and the nitrogen was fed at a flow rate of 10 ml per min. In this process Ba—X zeolite catalyst composite is replaced with Sr—X zeolites catalyst composite wherein the amount of catalyst was 2 g. The results so obtained are shown herein table 12 below.

TABLE 12

| | 1 hr | 2 hr | 3 hr | 4 hr |
|---|---|---|---|---|
| Product distribution (wt %) | | | | |
| Benzene | 0.021 | 0.01 | 0.011 | 0.01 |
| Toluene | 94.72 | 96.01 | 96.21 | 96.09 |
| Ethyl benzene | 0.01 | 0.01 | 0.01 | 0.01 |
| p-Xylene | 1.11 | 0.76 | 0.72 | 0.73 |
| m-Xylene | 0.90 | 0.68 | 0.65 | 0.67 |
| o-Xylene | 2.62 | 2.03 | 1.86 | 1.89 |
| Trimethyl benzene | 0.26 | 0.14 | 0.19 | 0.21 |
| Others | 0.34 | 0.35 | 0.33 | 0.38 |
| Performance (wt %) | | | | |
| Toluene conversion | 5.28 | 4.0 | 3.79 | 3.9 |
| Mixed xylene selectivity | 87.69 | 86.75 | 85.22 | 84.36 |
| p-Xylene selectivity | 23.97 | 21.90 | 22.29 | 22.19 |
| m-Xylene selectivity | 19.44 | 19.60 | 20.12 | 20.36 |
| o-Xylene selectivity | 56.59 | 58.50 | 57.59 | 57.45 |

Example 9: Preparation of the Alkylation Catalyst Composite (Sr—X Zeolite Catalyst Composite) Using Na—X Zeolites The Na—X zeolite was treated with 0.5 M of Strontium nitrate ($Sr(NO_3)_2$) solution using Step-I of Example 1 to obtain a Sr—X zeolite. In this process sodium nitrate is replaced with Strontium nitrate.

Preparation of Isomers of Xylene Using Sr—X Zeolite Catalyst Composite:

The isomers of xylene were prepared by employing the procedure described in the Example 1. Feed of toluene and methanol (4:1) with a weight hourly space velocity (WHSV) of 5.5 h$^{-1}$ was fed into pre-heater and the nitrogen was fed at a flow rate of 10 ml per min. In this process Ba—X zeolite catalyst composite is replaced with Sr—X zeolites catalyst composite wherein the amount of catalyst was 2 g. The results so obtained are shown herein table 13 below.

TABLE 13

|  | 1 hr | 2 hr | 3 hr | 4 hr |
| --- | --- | --- | --- | --- |
| Product distribution (wt %) | | | | |
| Benzene | 0.030 | 0.009 | 0.009 | 0.009 |
| Toluene | 97.45 | 97.99 | 97.95 | 98.03 |
| Ethyl benzene | 0.01 | 0.01 | 0.01 | 0.01 |
| p-Xylene | 0.50 | 0.40 | 0.43 | 0.41 |
| m-Xylene | 0.44 | 0.35 | 0.37 | 0.36 |
| o-Xylene | 1.164 | 0.94 | 1.00 | 0.96 |
| Trimethyl benzene | 0.13 | 0.09 | 0.09 | 0.09 |
| Others | 0.27 | 0.20 | 0.12 | 0.11 |
| Performance (wt %) | | | | |
| Toluene conversion | 2.55 | 2.01 | 2.05 | 1.97 |
| Mixed xylene selectivity | 82.51 | 84.08 | 87.80 | 87.82 |
| p-Xylene selectivity | 23.76 | 23.67 | 23.89 | 23.70 |
| m-Xylene selectivity | 20.91 | 20.71 | 20.56 | 20.81 |
| o-Xylene selectivity | 55.32 | 55.62 | 55.56 | 55.49 |

Example 10: Preparation of the Alkylation Catalyst Composite (Sr—X Zeolite Catalyst Composite) Using Na—X Zeolites The Na—X zeolite was treated with 0.5 M of Strontium nitrate (Sr(NO$_3$)$_2$) solution using Step-I of Example 1 to obtain a Sr—X zeolite. In this process sodium nitrate is replaced with Strontium nitrate.

Preparation of Isomers of Xylene Using Sr—X Zeolite Catalyst Composite:

The isomers of xylene were prepared by employing the procedure described in the Example 1. Feed of toluene and methanol (4:1) with a weight hourly space velocity (WHSV) of 1.0 h$^{-1}$ was fed into pre-heater and the nitrogen was fed at a flow rate of 10 ml per min. In this process Ba—X zeolite catalyst composite is replaced with Sr—X zeolites catalyst composite wherein the amount of catalyst was 2 g. The feed was contacted with the catalyst at a temperature of 380° C. The results so obtained are shown herein table 14 below.

TABLE 14

|  | 1 hr | 2 hr | 3 hr | 4 hr |
| --- | --- | --- | --- | --- |
| Product distribution (wt %) | | | | |
| Benzene | 0.01 | 0.017 | 0.016 | 0.017 |
| Toluene | 96.39 | 97.08 | 97.17 | 97.27 |
| Ethyl benzene | 0.01 | 0.003 | 0.003 | 0.004 |
| p-Xylene | 0.70 | 0.55 | 0.523 | 0.50 |
| m-Xylene | 0.60 | 0.49 | 0.47 | 0.45 |
| o-Xylene | 1.90 | 1.51 | 1.42 | 1.34 |

TABLE 14-continued

|  | 1 hr | 2 hr | 3 hr | 4 hr |
| --- | --- | --- | --- | --- |
| Trimethyl benzene | 0.16 | 0.13 | 0.13 | 0.13 |
| Others | 0.21 | 0.20 | 0.25 | 0.27 |
| Performance (wt %) | | | | |
| Toluene conversion | 3.61 | 2.92 | 2.83 | 2.73 |
| Mixed xylene selectivity | 88.64 | 87.33 | 85.27 | 83.88 |
| p-Xylene selectivity | 21.88 | 21.57 | 21.67 | 21.83 |
| m-Xylene selectivity | 18.75 | 19.22 | 19.48 | 19.65 |
| o-Xylene selectivity | 59.38 | 59.22 | 58.85 | 58.52 |

Example 11: Preparation of the Alkylation Catalyst Composite (Sr—X Zeolite Catalyst Composite) Using Na—X Zeolites The Na—X zeolite was treated with 0.5 M of Strontium nitrate (Sr(NO$_3$)$_2$) solution using Step-I of Example 1 to obtain a Sr—X zeolite. In this process sodium nitrate is replaced with Strontium nitrate.

Preparation of Isomers of Xylene Using Sr—X Zeolite Catalyst Composite:

The isomers of xylene were prepared by employing the procedure described in the Example 1. Feed of toluene and methanol (4:1) with a weight hourly space velocity (WHSV) of 1.0 h$^{-1}$ was fed into pre-heater and the nitrogen was fed at a flow rate of 10 ml per min. In this process Ba—X zeolite catalyst composite is replaced with Sr—X zeolites catalyst composite wherein the amount of catalyst was 2 g. The feed was contacted with the catalyst at a temperature of 460° C. The results so obtained are shown herein table 15 below.

TABLE 15

|  | 1 hr | 2 hr | 3 hr | 4 hr |
| --- | --- | --- | --- | --- |
| Product distribution (wt %) | | | | |
| Benzene | 0.09 | 0.09 | 0.22 | 0.31 |
| Toluene | 87.89 | 89.01 | 89.78 | 91.99 |
| Ethyl benzene | 0.03 | 0.05 | 0.07 | 0.08 |
| p-Xylene | 2.17 | 2.14 | 2.30 | 2.00 |
| m-Xylene | 1.97 | 1.89 | 2.00 | 1.76 |
| o-Xylene | 5.04 | 4.14 | 3.42 | 2.62 |
| Trimethyl benzene | 1.0 | 0.92 | 0.84 | 0.56 |
| Others | 1.7 | 1.73 | 1.34 | 0.65 |
| Performance (wt %) | | | | |
| Toluene conversion | 12.11 | 11.0 | 10.22 | 8.01 |
| Mixed xylene selectivity | 75.81 | 74.27 | 75.54 | 79.65 |
| p-Xylene selectivity | 23.64 | 26.19 | 29.79 | 31.35 |
| m-Xylene selectivity | 21.46 | 23.13 | 25.91 | 27.59 |
| o-Xylene selectivity | 54.90 | 50.67 | 44.30 | 41.07 |

Example 12: Preparation of the Alkylation Catalyst Composite (Sr—X Zeolite Catalyst Composite) Using Na—X Zeolites The Na—X zeolite was treated with 0.5 M of Strontium nitrate (Sr(NO$_3$)$_2$) solution using Step-I of Example 1 to obtain a Sr—X zeolite. In this process sodium nitrate is replaced with Strontium nitrate.

Preparation of Isomers of Xylene Using Sr—X Zeolite Catalyst Composite:

The isomers of xylene were prepared by employing the procedure described in the Example 1. Feed of toluene and methanol (4:1) with a weight hourly space velocity (WHSV) of 1.0 h$^{-1}$ was fed into pre-heater and the nitrogen was fed at a flow rate of 10 ml per min. In this process Ba—X zeolite catalyst composite is replaced with Sr—X zeolites catalyst composite wherein the amount of catalyst was 2 g. The feed was contacted with the catalyst at a temperature of 500° C. The results so obtained are shown herein table 16 below.

TABLE 16

|  | 1 hr | 2 hr | 3 hr | 4 hr |
| --- | --- | --- | --- | --- |
| Product distribution (wt %) | | | | |
| Benzene | 0.42 | 0.62 | 0.78 | 0.66 |
| Toluene | 88.62 | 89.85 | 91.46 | 92.31 |
| Ethyl benzene | 0.085 | 0.11 | 0.10 | 0.098 |
| p-Xylene | 2.71 | 2.55 | 2.18 | 1.99 |
| m-Xylene | 2.50 | 2.36 | 2.12 | 1.87 |
| o-Xylene | 3.65 | 2.84 | 2.25 | 2.12 |
| Trimethyl benzene | 0.94 | 0.72 | 0.51 | 0.43 |
| Others | 1.05 | 0.92 | 0.56 | 0.48 |
| Performance (wt %) | | | | |
| Toluene conversion | 11.32 | 10.15 | 8.54 | 7.7 |
| Mixed xylene selectivity | 78.27 | 76.35 | 76.70 | 77.66 |
| p-Xylene selectivity | 30.59 | 32.90 | 33.28 | 33.28 |
| m-Xylene selectivity | 28.22 | 30.45 | 32.37 | 31.27 |
| o-Xylene selectivity | 41.20 | 36.65 | 34.35 | 35.45 |

The embodiments herein and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results.

The numerical values given for various physical parameters, dimensions and quantities are only approximate values and it is envisaged that the values higher than the numerical value assigned to the physical parameters, dimensions and quantities fall within the scope of the invention and the claims unless there is a statement in the specification to the contrary.

While certain embodiments of the inventions have been described, these embodiments have been presented by way of example only, and are not intended to limit the scope of the inventions. Variations or modifications in the process or compound or formulation or combination of this invention, within the scope of the invention, may occur to those skilled in the art upon reviewing the disclosure herein. Such variations or modifications are well within the spirit of this invention. The accompanying claims and their equivalents are intended to cover such forms or modifications as would fall within the scope and spirit of the invention.

The invention claimed is:

1. A process for the preparation of isomers of xylene, said process comprising the following steps:
   i. obtaining an alkylation catalyst composite consisting of X-zeolite loaded with at least one metal ion, wherein said metal is selected from the group consisting of barium, strontium, and calcium;
   ii. activating the alkylation catalyst composite at a temperature of 450 to 650° C. for a time period of 30 minutes to 2 hours in a reactor to obtain an activated alkylation catalyst composite, wherein the temperature for activating the alkylation catalyst composite is attained by heating the reactor at a rate of 4 to 10° C. per minute; and
   iii. contacting the activated alkylation catalyst composite with toluene and methanol in the presence of an inert gas, at a temperature of 300 to 500° C. to obtain a reaction mixture comprising isomers of xylene, wherein a mass of ortho-xylene in said reaction mixture is greater than individual mass of para-xylene and meta-xylene.

2. The process as claimed in claim 1, wherein a weight ratio of toluene to methanol ranges between 1:1 and 4:1.

3. The process as claimed in claim 1, wherein a flow rate of toluene is maintained at a weight hourly space velocity of 1 per hour to 5 per hour of the activated alkylation catalyst composite.

4. The process as claimed in claim 1, wherein the inert gas is at least one selected from the group consisting of nitrogen, argon and helium.

5. The process as claimed in claim 1, wherein a flow rate of the inert gas ranges between 5 and 15 ml per minute.

* * * * *